United States Patent [19]
Wilding et al.

[11] Patent Number: 5,840,353
[45] Date of Patent: Nov. 24, 1998

[54] PROCESS FOR THE PREPARATION OF A FOOD PRODUCT

[75] Inventors: Peter Wilding, Wellingborough; Elizabeth Mary Woolner, Bedford, both of United Kingdom

[73] Assignee: Lipton, Division of Conopco, Inc., Englewood Cliffs, N.J.

[21] Appl. No.: 835,247

[22] Filed: Apr. 7, 1997

[30] Foreign Application Priority Data

Apr. 12, 1996 [EP] European Pat. Off. .............. 96302608

[51] Int. Cl.⁶ ................................ A23L 1/28; A01H 5/08
[52] U.S. Cl. ................................ 426/15; 426/50; 426/51; 426/52; 426/61; 426/599
[58] Field of Search ................................ 426/15, 50, 51, 426/52, 61, 49, 64, 599, 589

[56] References Cited

U.S. PATENT DOCUMENTS

| | | | |
|---|---|---|---|
| 2,534,263 | 12/1950 | Hills et al. ................................ | 99/103 |
| 3,976,805 | 8/1976 | Becker ................................ | 426/599 |
| 4,031,266 | 6/1977 | Mitchell et al. ................................ | 426/599 |
| 4,547,375 | 10/1985 | Mersfelder ................................ | 426/589 |
| 5,387,757 | 2/1995 | Bridges et al. ................................ | 800/205 |

FOREIGN PATENT DOCUMENTS

| | | |
|---|---|---|
| 480 422 | 4/1992 | European Pat. Off. . |
| 94/12055 | 6/1994 | WIPO . |
| 94/25575 | 11/1994 | WIPO . |
| 94/28745 | 12/1994 | WIPO . |
| 95/11600 | 5/1995 | WIPO . |
| 97/10726 | 3/1997 | WIPO . |
| 97/10727 | 3/1997 | WIPO . |

OTHER PUBLICATIONS

*High Pressure and Biotechnology*, Colloque INSERM/1992, vol. 24 pp. 195–209.
*Anal. Biochem* 47:273–279, (1972) (Lever M.).
*J. Sci. Food Agric* 33:365–372 (1982), Nicolas.
*In Flavour Science*, ACS 259–286, 1993, Buttery.
Industria Conserve 70, 1995, pp. 119–127, Castaldo et al.
Industria Conserve 70, 1995, pp. 253–258, Castaldo et al.
Dissertation Abstracts International, DA8911927, 50, Sep. 1989, Jones.
J. Food Sci., 60, pp. 1277–1281, Marangoni et al. 1995.

*Primary Examiner*—Cynthia L. Nessler
*Attorney, Agent, or Firm*—Gerard J. McGowan, Jr.

[57] ABSTRACT

A process for providing a tomato-based product comprising the following steps: a) applying ultra high pressure to a tomato piece, such that polygalacturonase is inactivated and pectinmethylesterase and preferably peroxidase are not inactivated; b) incubating the tomato piece with endogenous pectinmethylesterase to achieve a desired consistency and preferably with peroxidase to achieve a fresh aroma and/or flavour profile; and c) inactivating the pectinmethylesterase and any peroxidase.

3 Claims, No Drawings

PROCESS FOR THE PREPARATION OF A FOOD PRODUCT

FIELD OF THE INVENTION

The invention relates to a process for the preparation of tomato-based products of high quality and consistency and products obtained by this process.

BACKGROUND TO THE INVENTION

It is desirable to be able to produce tomato-based products having a high consistency and quality with a low solids content. In order to do this, it is necessary to be able to substantially increase the viscosity of the tomato pastes commonly used to prepare products such as sauces.

It is also desirable to be able to produce tomato-based products having a fresh, rather than a processed, flavour and/or aroma profile.

Enzymes, such as polygalacturonase (PG) and pectinmethylesterase (PME), are naturally-present in tomatoes. If the tomatoes are broken-down, these enzymes are released and pectinmethylesterase catalyses the removal of methyl ester groups from pectin molecules occurring naturally in the tomatoes, thereby producing pectic and pectinic acids; polygalacturonase rapidly depolymerises these pectic and pectinic acids. Consequently, the tomato-based product lacks pectic substances and has a thin and watery consistency.

Heating a paste of broken-down tomatoes above 80° C. inactivates PME and PG, thereby preventing breakdown of pectic substances in tomato products during processing, such that a good consistency is maintained. However, heating leads to increased rates of chemical reactions including the Maillard reaction, , lad to the browning of tomato products and the generation of off-flavours.

High Pressure and Biotechnology, Colloque INSERM/ 1992, Vol 24 pp 195–209 discusses the effects of high pressure (1–7 kbar) on enzymes. It states that polyphenoloxidase does not appear to be inactivated by UHP. It also mentions the conditions necessary to inactivate PME in citrus fruits, and concludes that pressurisation conditions sufficient for the microbial 'pasteurisation' of fruit juices or purees do not fully stabilise them against modifications by PME and some other enzymes. These 'pressure-pasteurised' acid foods therefore also require a mild thermal blanching, a refrigerated storage or the addition of enzyme inhibitors, to fully inactivate the degrading enzymes. Enzyme inactivation is important for achieving long term ambient stability.

The present invention seeks to provide a process for manipulating the consistency and texture of tomato-based products having a low solids content. Preferably, the tomato-based product has a flavour/aroma profile and a colour which is perceived as fresher than conventionally processed tomato-based products.

SUMMARY OF THE INVENTION

According to the present invention there is provided a process for providing a tomato-based product, comprising the following steps:

a) applying ultra high pressure to a tomato piece, such that polygalacturonase is inactivated and pectinmethylesterase is not inactivated;

b) incubating the tomato piece with endogenous pectinmethylesterase to achieve a desired consistency; and c) inactivating the pectinmethylesterase.

The inventors of the present invention were surprised to find that under suitable conditions, polygalacturonase is inactivated by applying ultra-high pressure (UHP), whereas pectinmethylesterase remains active. For example, applying a pressure of 500 MPa for 15 minutes at approximately 20° C. achieves this selective inactivation of PG.

In the absence of polygalacturonase to depolymerise the pectic and pectinic acids formed by the action of PME on pectin, these acids remain in the cell wall to prevent structural breakdown. The selective inactivation of polygalacturonase may therefore prevent texture degradation.

Also, incubating the tomato piece with endogenous PME in step b results in a firming effect and an improvement in texture. This is because the removal of methyl ester groups from pectin molecules, catalysed by PME, results in the pectin molecules being able to associate with each other via cation cross-links to provide an increase in consistency. The incubation may be conducted at 42° C. for 30 minutes.

Once the desired thickness has been achieved, the PME is inactivated by, for example, heating, adjusting pH and/or adding inhibitors. If heating is used, the temperature is typically raised to 90° C. for 10 minutes. Such a heat treatment is sufficient to pasteurise the product. Hence, a single heating step may be used both to inactivate PME and to pasteurise, resulting in a treatment which requires less heat input in comparison to the use of separate inactivation and pasteurisation heating steps.

The inventors have also found that, under certain UHP conditions, the enzyme peroxidase remains active together with PME after PG has been inactivated. They have found that peroxidase is more stable to UHP than PG, but less stable than PME. In contrast, the inventors have found that peroxidase is less heat stable than both PG and PME; therefore, peroxidase is inactivated before PG and PME in the heat treatments of the processes conventionally used for preparing tomato products.

Without wishing to be bound by theory, the inventors believe that peroxidase is important in the generation of volatiles for providing a fresh tomato flavour/aroma profile, and that the presence of active peroxidase in the tomato product during the incubation step b is advantageous to the perception of freshness in the final tomato product. The process of the present invention may therefore result in a tomato product having a flavour/aroma profile which is perceived as fresher than conventionally processed tomato products, since peroxidase is inactivated relatively quickly during the heating of conventional processes.

In the present invention, any active peroxidase is inactivated in step c, together with PME, thus preventing the flavour and/or aroma effects developing to extremes and decreasing quality.

A tomato piece is, for example, whole tomatoes either peeled or unpeeled, or a piece of chopped, diced, comminuted or macerated tomato. The tomato piece may have a size in the range of from approximately 10 µm to approximately 10 cm and may form part of a tomato paste, puree or juice. Commonly, the present invention is applied to a plurality of tomato pieces simultaneously.

An advantage of the process of the present invention is the manipulation of the viscosity and texture of tomato-based products. Once PG has been inactivated using UHP, viscosity and texture is controlled by the conditions of the incubation step b and the inactivation step c; ie. they control the degree of firming which occurs. Moreover, using the process of the present invention, the tomato-based products preferably have a flavour/aroma profile and/or a colour which is perceived as fresher than conventionally processed tomato-based products. Therefore, by selecting the right conditions for steps a, b and c, viscosity and/or texture improvement, and preferably fresh colour, flavour and/or aroma generation, can be achieved.

Thus, the present invention provides means for selectively inactivating deleterious enzymes, and for maintaining and promoting the activity of other enzymes to control and improve viscosity and texture, and, preferably, also to improve colour, flavour and/or aroma.

Examples of the products and processes of the invention will now be described to illustrate, but not to limit, the invention.

DETAILED DESCRIPTION OF THE INVENTION

EXAMPLE 1

Eight 150 g samples of tomato dice were subjected to a range of ultra high pressures for different lengths of time using a high hydrostatic pressure unit. The pressure and time treatments used are listed in Table 1.

Pressure, up to a maximum of 600 MPa, was provided by water pumped into the base of the unit. Water was used as the pressure transferring medium. Generally, it took 2–3 minutes for the UHP system to reach the chosen pressure. It also took 2–3 mins to depressurize after treatment. The pressure and temperature, measured at four points within the unit, were logged continuously by a computer. All experiments were carried out at ambient temperature.

A portion of each pressure-treated sample was stored for analysis either by freezing it rapidly using dry ice and storing at −20° C. or by packing it in 150 g of tomato juice in foil pouches, heat sealing the pouches and heat treating for 30 minutes in a waterbath set at 97° C. This heat treatment was sufficient to inactivate all enzymes and to achieve pasteurisation.

The remainder of each pressure-treated sample was placed in a sachet and incubated for 30 minutes in a waterbath set at either 40° C. or 60° C.

These samples were also stored for analysis, using the method described above.

For each stored sample, the activity of the enzymes pectin methyl esterase (PME), polygalacturonase (PG), lipoxygenase and peroxidase was determined using methods i to iv described below. The activity of these enzymes was also measured in a sample of the tomato dice which had not undergone the pressure and thermal incubation treatments described above (this was the control sample).

i) PME activity was assayed by adding 200 μl of sample to 20 mls 1% apple pectin in 0.15M sodium chloride (pH 7.5 with sodium hydroxide). Activity was calculated from the slope of mls 0.025M NaOH used to maintain pH 7.5 at 30° C. against time.

ii) PG activity was measured by the detection of reducing ends, which are generated when the enzyme breaks down polygalacturonic acid, using the calorimetric PAHBAH assay (Lever M. (1972) Anal Biochem 47: 273–279). PAHBAH is an abbreviation of the chemical p-hydroxybenzoic acid hydrazide, which is used for the colour detection of reducing sugars. A high salt extract was prepared by adding low salt buffer (25 mM sodium acetate buffer pH 5.6) to a tomato sample at a ratio of 1:2 volume:weight, shaking vigorously then centrifuging at 10,000 g for 20 minutes at 4° C. After centrifugation, the supernatant was poured away and the pellet resuspended in an equivalent volume of a high salt buffer (25 mM sodium acetate buffer pH 5.6 containing 1.0M sodium chloride) and left to stand at 4° C. for 1 hour. The suspension was then respun at 10,000 g, 4° C. for 20 minutes and the supernatant (high salt extract) stored at −70° C. in 1 ml aliquots.

For PG assays, the high salt extract was diluted 1:100 in 50 mM sodium acetate buffer pH 4.0 containing 0.2M NaCl; the activity was assayed using 0.2% polygalacturonic acid in a total assay volume of 500 μl. The assays were incubated at 40° C. for 1 hour and terminated by generating colour, which comprised adding 5 mls of PAHBAH reagent and boiling for 6 minutes. After cooling under running water to room temperature, absorbance was read at 410 nm using quartz cuvettes against a standard curve of galacturonic acid. Controls were performed by terminating assays with PAHBAH reagent as soon as the enzyme extract was added, ie. at zero time, and boiling as above.

iii) Lipoxygenase activity was determined at 30° C. using the polarographic method of Nicolas et al (1982 J. Sci Food Agric 33:365–372) using linoleic acid (28 mM final concentration) dispersed in 0.1M sodium phosphate buffer pH 7.0 containing polyoxyethylenesorbitan monolaurate (0.8% final concentration) in a total volume of 5 ml.

iv) Peroxidase activity was determined by the spectrophotometric quantification of o-quinone production in a mixture containing 3.0 μl 30% hydrogen peroxide (8.8 mM final concentration), phosphate buffer pH 7.0 and enzyme extract, in a total volume of 2.925 ml. The reaction was initiated by adding 0.075 ml of guaiacol (5 mM final concentration) and measuring the change in absorbance at 400 nm using a spectrophotometer with a temperature controlled cuvette holder at 30° C.

The results of these measurements for each sample after pressure-treatment alone are shown in Table 1 below.

TABLE 1

| | % activity remaining after treatment | | | |
| --- | --- | --- | --- | --- |
| Treatment | PME | PG | Lipoxygenase | Peroxidase |
| 300 MPa, 5 min | 100 | 100 | — | — |
| 300 MPa, 15 min | 100 | 99 | — | — |
| 400 MPa, 10 min | 100 | 100 | 74 | 96 |
| 400 MPa, 20 min | 100 | 62 | 51 | 79 |
| 500 MPa, 10 min | 100 | 3 | 1 | 77 |
| 500 MPa, 20 min | 100 | 0 | 0 | 71 |
| 600 MPa, 10 min | 100 | 0 | 0 | 5 |
| 600 MPa, 20 min | 100 | 0 | 0 | 0 |

The results of these measurements for samples after pressure-treatment alone and after both pressure-treatment and thermal incubation are shown in Table 2 below, together with the results for the control sample.

TABLE 2

| | % activity remaining after treatment | | | |
| --- | --- | --- | --- | --- |
| Treatment | PME | PG | Lipoxygenase | Peroxidase |
| No treatment (control) | 100 | 100 | 100 | 100 |
| 400 MPa 10 mins | 100 | 100 | 74 | 96 |
| 400 MPa 10 mins + 40° C. 30 mins | 90 | 76 | 33 | 100 |
| 400 MPa 10 mins + 60° C. 30 mins | 58 | 45 | 0 | 100 |
| 600 MPa 20 mins | 100 | 0 | 0 | 0 |
| 600 MPa 20 mins + 40° C. 30 mins | 86 | 0 | 0 | 0 |
| 600 MPa 20 mins + 60° C. 30 mins | 72 | 0 | 0 | 0 |

The results in Table 1 show that PME is the most barostable enzyme. Its activity is not affected after a pressure treatment of 600 MPa for 20 minutes. Peroxidase is the next most stable enzyme, followed by PG and lipoxygenase, which have similar stabilities. After a pressure treatment of 500 MPa for 20 mins, both PME and peroxidase are active whilst PG and lipoxygenase have been inactivated; the presence of peroxidase is favourable to flavour and aroma.

From Table 2, it is clear that there are pressures which inactivate PG, lipoxygenase and peroxidase but do not inactivate PME. Subsequent incubation allows the active PME to promote firming in the absence of PG-promoted texture degradation, as evidenced by example 2 below.

EXAMPLE 2

In accordance with the methods of example 1, tomato juice samples were treated with UHP (either 400 MPa for 10 mins which is not sufficient for PG inactivation or 600 MPa for 20 mins which is sufficient for PG inactivation) and incubated at either 40° or 60° C. for 30 mins. Samples were then pasteurized by filling into foil pouches, heat sealing and placing in a waterbath at 95° C. for 30 minutes. All enzyme activities were inactivated after this pasteurising heat treatment.

The effects of the pressure and incubation treatments on the consistency of the tomato juice were measured by determining the serum to pellet ratio and the Bostwick value of the treated tomato juice. The serum to pellet ratio and Bostwick value were also determined for non-treated tomato juice, as a control.

Serum to pellet ratio is a measure of the volume occupancy of the insoluble solids component of tomato juice and was determined by centrifuging the juice (3000 g, 10 minutes) and then weighing the resultant serum (solubles) and pellet (insolubles) fractions to determine the ratio. The higher the level of insolubles (ie the lower the serum to pellet ratio), the thicker the sample and the higher its consistency.

Bostwick is the standard industry measurement for tomato product viscosity. To obtain juice Bostwick values, the serum was removed from the pellet by centrifugation as above and then added back to 70% of the original sample weight. The measurements were made in a standard Bostwick viscometer. The sample was placed in the levelled viscometer, the shutter opened and a timing clock started.

The distance (in centimetres) at 20° C. over which the sample flowed in 30 s was recorded. The lower the Bostwick value, the thicker the sample and the higher its consistency.

The serum to pellet ratios and the Bostwick values determined are shown in Table 3.

TABLE 3

| Treatment | Serum:pellet | Bostwick (cm) |
|---|---|---|
| No treatment (control) | 3.2 | 8.1 |
| 400 MPa 10 mins + 40° C. 30 mins | 2.7 | 10.1 |
| 400 MPa 10 mins + 60° C. 30 mins | 2.8 | 10.3 |
| No treatment (control) | 2.8 | 8.8 |
| 600 MPa 20 mins + 40° C. 30 mins | 1.4 | 6.1 |
| 600 MPa 20 mins + 60° C. 30 mins | 1.2 | 5.9 |

From this example and example 1, the following conclusions can be drawn.

Tomato juice given a UHP treatment of 400 MPa for 10 minutes still has 100% of its PG activity remaining (Table 1). Even after a thermal incubation of 60° C. for 30 mins there is still 45% PG activity remaining (Table 2). During the mild thermal incubation this remaining activity is able to depolymerize pectin in the juice which is reflected in the higher Bostwick values and serum to pellet ratios (ie lower consistencies) of the treated samples.

Tomato juice given a UHP treatment of 600 MPa for 20 minutes has no PG activity remaining after treatment (Table 1). However PME is unaffected by this treatment and during the mild thermal incubation PME activity is stimulated (PME has a temperature optimum close to 60° C.) to catalyse the removal of methyl ester groups from pectin molecules resulting in the pectin molecules being able to associate with each other via cation cross-links to provide a decrease in Bostwick values and serum to pellet ratios, ie. an increase in consistency.

EXAMPLE 3

The juice colours of the final samples of example 2 were measured using an Ultrascan XE™; this is a machine for measuring colour available from Hunterlab, USA. The measurements are shown in Table 4 below; the values given are the ratios of the Hunterlab "a" and "b" scores; these scores are used by Hunterlab to describe food colour; "a" is a red to green scale; "b" is a yellow to blue scale.

TABLE 4

| Treatment | a/b ratio |
|---|---|
| No treatment (control) | 1.89 |
| 400 MPa 10 mins + 40° C. 30 mins | 1.96 |
| 400 MPa 10 mins + 60° C. 30 mins | 1.85 |
| 600 MPa 20 mins + 40° C. 30 mins | 2.00 |
| 600 MPa 20 mins + 60° C. 30 mins | 1.93 |

From these results it can be concluded that UHP treatment in combination with mild thermal incubation has very little effect on tomato colour. This is beneficial as it is desirable to retain as much of the original fresh tomato red colour as possible in the final product. In contrast, the prior art heat processes lead to the generation of brown colours due to the Maillard reaction.

EXAMPLE 4

A sample of 150 g of tomato dice was subjected to a pressure of 500 MPa for 15 mins, incubated in a water bath for 30 mins at 42° C. and pasteurised, all in accordance with the method of example 1. Qualitative volatile analysis was then carried out on the sample using a Tekmar™ dynamic headspace (purge & trap) apparatus (model LSC2000 available from Interscience). Four grams of the sample was purged for 10 minutes with helium at 45° C. The volatiles were trapped on Tenax™ absorbing material and cryofocussed before injection into a gas chromatograph. Qualitative information was obtained by means of a dual column system, using chromatography columns of differing polarities (namely models CPSil05 and CPSil13 available from Chrompack), and a reference database. Semi-quantitative information was obtained by comparing peak heights and areas. This analysis was also carried out on a sample of untreated tomato dice pasteurised in tomato juice, as a control.

Relative peak heights for selected volatiles in the samples are shown in Table 5. 3-methylbutanal, hexanal, cis-3- hexenal and 6-methyl-5-hepten-2-one are important for both fresh and processed tomato aroma (Buttery RG, 1993, In Flavour Science: Sensible Principles and Techniques, ACS, 259–286). Cis-3-hexen-1-ol is important for fresh tomato aroma.

TABLE 5

| Volatile | Peak height relative to untreated control | |
| --- | --- | --- |
|  | untreated (control) | UHP 500 MPa 15 mins + 42° 30 mins |
| 3-methylbutanal | 100 | 135 |
| 2-methylbutan-1-ol | 100 | 100 |
| hexanal/cis-3-hexenal | 100 | 350 |
| cis-3-hexen-1-ol | 100 | 125 |
| 1-hexanol | 100 | 125 |
| 6-methyl-5-hepten-2-one | 100 | 150 |

This shows that the UHP treatment resulted in an increase in 3-methylbutanal, hexanal, cis-3-hexenal, cis-3-hexen-1-ol, 1-hexanol and 6-methyl-5-hepten-2-one.

It can be concluded from Table 1 that a UHP treatment of 500 MPa for 15 minutes is sufficient to inactivate PG, but not sufficient to inactivate peroxidase or PME. Without wishing to be bound by theory, the inventors believe that the presence of peroxidase during the incubation step is responsible for the generation of free radicals which may be involved in the oxidation of lipids and carotenoids, to generate most of the volatiles listed in Table 5.

The results of this experiment show that UHP treatment can be used to produce tomato dice with altered aroma volatile profiles.

We claim:

1. A process for providing a tomato-based product comprising the following steps:

a) applying ultra high pressure to a tomato piece, such that polygalacturonase is inactivated and pectinmethylesterase is not inactivated;

b) incubating the tomato piece with endogenous pectinmethylesterase to achieve a desired consistency; and c) inactivating the pectinmethylesterase.

2. A process as claimed in claim 1, wherein, in step a, peroxidase is not inactivated.

3. A process as claimed in claim 2, wherein, in step c, peroxidase is inactivated.

* * * * *